(12) United States Patent
Favre (10) Patent No.: US 11,819,599 B2
(45) Date of Patent: Nov. 21, 2023

(54) EXTRACORPOREAL BLOOD CIRCULATION DEVICE

(71) Applicant: Infomed SA, Meinier (CH)

(72) Inventor: Olivier Favre, Thônex (CH)

(73) Assignee: INFOMED SA, Meinier (CH)

(*) Notice: Subject to any disclaimer, the term of this patent is extended or adjusted under 35 U.S.C. 154(b) by 368 days.

(21) Appl. No.: 17/117,736

(22) Filed: Dec. 10, 2020

(65) Prior Publication Data

US 2021/0178049 A1    Jun. 17, 2021

(30) Foreign Application Priority Data

Dec. 11, 2019 (EP) .................................. 19215310

(51) Int. Cl.
    *A61M 1/36*      (2006.01)
    *A61L 33/04*      (2006.01)
    *A61L 33/12*      (2006.01)

(52) U.S. Cl.
    CPC ........... *A61M 1/3672* (2013.01); *A61L 33/04* (2013.01); *A61L 33/128* (2013.01); *A61M 2205/3331* (2013.01); *A61M 2205/3334* (2013.01); *A61M 2205/502* (2013.01); *A61M 2205/52* (2013.01)

(58) Field of Classification Search
    CPC ....... A61K 38/00; A61L 33/04; A61L 33/128; A61M 1/3672; A61M 2202/045; A61M 2205/3331; A61M 2205/3334; A61M 2205/502; A61M 2205/52
See application file for complete search history.

(56) References Cited

U.S. PATENT DOCUMENTS

2012/0273415 A1* 11/2012 Gerber .................. B01D 61/00
                                                            210/741
2015/0374897 A1* 12/2015 Favre .................. A61M 1/3465
                                                            210/96.1

FOREIGN PATENT DOCUMENTS

EP           1095666         5/2001

OTHER PUBLICATIONS

Calatzis et al., "Citrate Anticoagulation for Extracorporeal Circuits: Effects on Whole Blood Coagulation Activation and Clot Formation", Nephron, Oct. 2001, vol. 89, pp. 233-236 (4 pages).

(Continued)

*Primary Examiner* — Dirk R Bass
(74) *Attorney, Agent, or Firm* — NIXON & VANDERHYE (57) ABSTRACT

Disclosed is an extracorporeal blood circulation device including a blood circulation circuit including a blood extraction line and a return line, a blood circulator in the circulation circuit and a control unit including a calculator arranged determining at least one parameter, recording it in a memory, and then comparing the standard value of the parameter with the recorded value. The device also includes a source of solution for liquefying blood clots, a device injecting and conveying the liquefaction solution in the circulation circuit, the control unit including a driver for the injector of the liquefaction solution. The control unit is arranged to actuate the driver when the value is exceeded, meaning that at least one clot has formed, the driver being arranged so that the liquefaction solution is present in the circulation circuit in an amount and for a time determined to be sufficient for liquefying the clot formed.

20 Claims, 3 Drawing Sheets

(56) References Cited

OTHER PUBLICATIONS

Quencer et al., "Hemodialysis access thrombosis, review article", Cardiovascular Diagnosis & Therapy, Dec. 2017; vol. 7, Supplement3, S299-S308 (10 pages).
Search Report for EP 19 21 5310 dated Aug. 17, 2018, 4 pages.
Calatzis et al., "Citrate Anticoagulation for Extracorporeal Circuits: Effects on Whole Blood Coagulation Activation and Clot Formation", Nephron, 2001, vol. 89, No. 2, pp. 233-236.
Quencer et al., "Hemodialysis access thrombosis", Cardiovasc Diagn. Ther. 2017 (Suppl 3), Dec. 2017, pp. S299-S308.
Kennard et al., "Interventions for treating central venous haemodialysis catheter malfunction (Review)", Cochrane Database of Systematic Reviews, Oct. 26, 2017, Issue 10, 53 pages.

* cited by examiner

EXTRACORPOREAL BLOOD CIRCULATION DEVICE

CROSS-REFERENCE TO RELATED APPLICATIONS

This application claims priority to EP 19215310.4 filed Dec. 11, 2019, the entire contents of each of which are hereby incorporated by reference.

BACKGROUND OF THE INVENTION

Field of the Invention

The present invention relates to an extracorporeal blood circulation device having an extracorporeal blood circulation circuit.

Description of the Related Art

Devices for performing extracorporeal blood circulation exist and are widely described in the literature; they perform numerous functions, for example extracting blood components (white blood cells, plasma, platelets, etc. referred to hereinbelow as "apheresis"), for treating patients having a pathology requiring a blood purification, such as kidney failure (haemodialysis, haemofiltration, haemodiafiltration, referred to hereinbelow as "dialysis"), for providing blood circulation during heart surgery (referred to hereinbelow as "ECC") or for blood oxygenation (referred to hereinbelow as "ECMO"). Dialysis, ECCs and ECMO are always for therapeutic purposes, i.e. for treating patients, whereas apheresis is either aimed at patients having, for example, an autoimmune disease or hypercholesterolaemia, or at donors who are healthy individuals donating components from their blood such as plasma, platelets or red blood cells. Various blood circulation systems are available to achieve this, which all include tubing for circulating the blood, and pumps for establishing a flow, for instance peristaltic pumps, centrifugal pumps or diaphragm pumps. The various means known for circulating blood outside the patient by forming an extracorporeal circulation circuit (referred to hereinbelow as a "circuit") have been described in the literature for over 40 years; all have in common the activation of blood coagulation via two main mechanisms, namely placing the blood in contact with substances such as plastic or air, and turbulent or variable-pressure flows which result from the configuration of the circuits.

Blood coagulation is achieved by a cascade of events, many of which are still poorly understood, and which can be summarized, in a simple manner, as follows: the platelets present in the blood are first activated, i.e. put in a state where they can easily bind, when facing an unusual situation such as contact with an unknown material or a strong and sudden variation in pressure. They then agglutinate to form a "platelet plug", typically made for closing a wound such as in the case of a skin cut. This plug is then strengthened by various coagulation factors, notably fibrinogen, in order to become a "fibrin plug". While this phenomenon is desirable for stopping a haemorrhage in the case of a bleeding wound, it must be avoided in blood circulation circuits as it reduces the capacity of the circuit to circulate the blood, ending up by stopping it altogether, thus rendering said circuit unusable.

The coagulation cascade interacts with that of inflammation and that of immunity, both of which are also often altered during the period of circulation in the circuit, either directly due to the treatment being performed, for example when said treatment removes inflammation mediators or antibodies, or due to external factors, for instance the use of antibiotics; the coagulation cascade parameters are thus liable to be modified not only due to the blood passing in the circuit but also due to the patient's situation over the duration of the circulation, which may be several days, or even weeks. Numerous phenomena are thus involved to coagulate blood, or, on the contrary, to prevent its coagulation, and it would be fanciful to imagine being aware of them all in order to prevent any coagulation in a circuit. Therefore, despite all the means deployed to date, blood coagulation in extracorporeal circulation circuits remains one of the main reasons for undesired circuit changing, which is done by stopping the device, after having, where possible, returned the blood to the patient/donor, and then installing a new circuit and preparing the device with "priming" and "rinsing" phases. When this happens, it is not always possible to return the blood to the patient, who then loses an appreciable amount possibly necessitating a blood transfusion, particularly when the situation occurs several times in less than 48 hours. In the most serious clinical cases, the extracorporeal circulation is performed in a continuous manner, defined as being round-the-clock without interruption until the clinical situation of the patient makes it no longer required, which may often be a matter of days or weeks. Stopping the extracorporeal circulation due to blood coagulation in the circulation circuit may thus have various negative effects depending on the function provided. For example, in the case of dialysis, stopping the blood circulation due to its coagulation in the circuit may lead to a loss of blood which is tolerable in itself, albeit rare; in this case, the treatment will simply be continued after a circuit change. In the case of heart (ECC) and/or lung (ECMO) replacement, stopping the circulation may lead to the death of the patient within minutes if no emergency surgery is performed, such surgery being major and not being without risks of failure. In all cases, changing the circuit takes at least 30 minutes, exposes the patient to certain risks and is materially expensive. It is thus essential for the circuit to be able to work without interruption, even in the case of blood coagulation.

In practice, it is common for blood to coagulate in the extracorporeal circulation circuits, which takes place within a few seconds, or even 1 or 2 minutes. II is therefore not unusual to find small clots that will mainly be found in the blood clot filter which is placed at the outlet of the circuit and designed to collect them. However, with the growth of the clots being exponential by nature, they may get larger and become big enough to greatly reduce or even block the circulation anywhere in the circuit, mostly in the purification member or the blood clot filter.

To prevent this, it is known practice to use, as a preventive measure, substances defined as being anticoagulant; various widely described means are thus used on a daily basis, mainly injection of heparin or of citrate into the blood circuit. When it is necessary and possible, notably due to the low content of platelets in the blood, blood circulation in the circuit may also be performed without such preventive anticoagulation.

Heparin, whose role is to activate antithrombin III, is generally used for systemic anticoagulation, i.e. the patient/donor's blood which is anticoagulated in the circuit stays in that state as it is being returned to the patient, which leads, amongst other things, to haemorrhage risks for said patient. Therefore, the use of heparin is often not recommended for patients who have undergone surgery, including a simple biopsy, within 24 hours prior to the extracorporeal treatment.

Citrate binds to ionized calcium ($Ca^{++}$), an indispensable element in the coagulation cascade, which cannot take place without it. It has thus been demonstrated, in the publication by Calatzis et al., "Citrate anticoagulation for extracorporeal circuits: Effects on whole blood coagulation activation and clot formation"; Nephron 2001; 89:233-236, that an ionized calcium ($Ca^{++}$) concentration in the blood of less than 0.4 mmol/L of blood increases the coagulation time, the curve being exponential and the blood ceasing to coagulate at a concentration of ionized calcium ($Ca^{++}$) in the blood of less than 0.2 mmol/L. Therefore, the injection of citrate into the blood circulating in the extracorporeal circuit has been put into clinical use and is widely described in the literature, as it has, compared to heparin, the benefit of acting only in the circuit; specifically, after running through a few centimetres of the patient's vein, the blood from the circuit regains, by mixing with the patient's blood which has contents of 0.9-1.1 mmol/L, an ionized calcium concentration of greater than 0.5 mmol/L, which immediately stops the anticoagulant effect of citrate. This is then referred to as "regional anticoagulation" since it is limited to the extracorporeal circulation circuit, which makes it possible to avoid the haemorrhage risks for the patient and to increase the time of use of the extracorporeal circulation circuit, at least in the most frequent cases where citrate is well tolerated by the patient.

Another technique for reducing coagulation in the circuit consists in diluting the blood, and thus the platelet concentration, which is achieved by the injection, at the start of the circuit, of a crystalline physiological solution, known as predilution; in order to be efficient, said method requires large amounts of solution which needs to be removed before returning the blood to the patient, to avoid a fluid overload. Therefore, this method is only applicable to haemofiltration and usually comes in addition to the techniques described above. Furthermore, it has the drawback of reducing the efficiency of the treatment, as the treated blood is diluted and thus contains fewer components to be removed.

In the above three cases of preventive anticoagulation treatments, the injected amount of solution for preventing coagulation is the result of an optimum. In the case of heparin, a balance between anticoagulation in the circuit and haemorrhage risks for the patient must be found. Citrate, which binds to life-essential ions such as $Ca^{++}$, may induce imbalances leading to disastrous clinical situations, or even death, since the blood returned to the patient has an ionized calcium concentration of from 0.2 to 0.4 mmol/L, a value lower than 0.6 mmol/L being lethal. Specifically, depending on the situation, the cumulative dose of citrate may gradually lower the ionized calcium concentration in the patient and bring it below 0.6 mmol/L. Predilution, for its part, must be optimized to avoid diluting the blood which in turn is liable to reduce the treatment capabilities below the desirable threshold.

Therefore, dosing of the injected fluids for preventive anticoagulation purposes is the fruit of a subtle and empirical balance, which moreover fluctuates over the time the blood circulates in the circuit. Thus, it frequently arises that the preventive anticoagulation of the blood in the circuit is insufficient and that the blood coagulates regardless, thus stopping the circulation in the circuit, but also that the anticoagulation is too substantial and becomes a source of risk for the patient. This is all the more true since the choice of the flow rates of the preventive anticoagulation solutions comes under the responsibility of the nursing staff, who adapt it according to the development of the situation, that existing in the circuit but also that of the clinical state of the patient, both often progressing in a rapid manner, i.e. within minutes. Another practical difficulty arises from the fact that there is a delay of response between correcting the injection rates and the result of these corrections, which can only be checked after a period of several minutes or even hours, i.e. representing a period during which the nursing staff will perform a great number of other tasks and will let a time elapse, which will entail added risks of coagulation in the circuit. Moreover, system parameters, such as the effective blood flow rate, the presence of air in the circuit, shutdowns of the blood pump due to alarms or haemo-concentrations, vary in a random manner and all, without any possibility for anticipation, have a great influence on the possible occurrence of clots in the circuit. Therefore, it is impossible, except by using preventive injections of massive, poorly tolerated doses of anticoagulant, to avoid in all cases coagulation in the circuit, which is confirmed in practice on a daily basis.

Moreover, it is known that, for the various forms of heparin, the best methods for evaluating the anticoagulation achieved, which are measurements of the coagulation time performed by devices designed to provide standardized data, are not predictive of blood coagulation in the circulation circuit with 100% reliability. The same applies for citrate, as blood sometimes coagulates due to the limits imposed by the patient's tolerance towards an injection of citrate and their variation with time. In any case, it is thus possible that the blood present in the circulation circuit coagulates, despite the implementation of prevention means, this being a gradual phenomenon which can take from a few minutes to a few tens of minutes. Therefore, regardless of the substance used for the preventive anticoagulation, the lack of efficiency is mainly due to having to minimize the amount of substance, which of course increases the risk of blood coagulation in the circuit; this is observed on a daily basis in care units and leads either to stoppage of the treatment under way, with eventual resumption after setting up a new circuit, or stoppage of the treatment associated with the patient's blood loss which is often equivalent to the blood volume of the extracorporeal circulation circuit (between 200 ml and 2 litres), or to major complications due to shutting down the central circulation and/or the oxygenation of the patient's blood.

Therefore, it appears that it would be advantageous to be able to liquefy, i.e. dissolve, the coagulated (solidified) blood in a circuit, in order for it to be fluid again and to avoid the problems described above. The literature mentions "fibrinolysis" which is described as an enzymatic liquefaction of fibrin clots and "thrombolysis", or fibrinolysis therapy, which consists in liquefying clots present in blood vessels. Clot liquefaction systems have been described and are used for laboratory analyses or for unclogging vessels following strokes, and thus restoring the blood flow in the patient, by means of a chemical method or sound waves. Fibrinolysis is thus documented in the context of pathologies involving the formation of clots in the body, such as coronary syndromes, pulmonary embolism or myocardial infarction. Specifically, the undesirable coagulation observed in extracorporeal circulation circuits may also take place in the human body and block the blood circulation in a similar manner. A natural fibrinolysis system exists, which dissolves clots and usually prevents, amongst other things, the above-mentioned pathologies. When the functioning of this system is no longer satisfactory, drugs may be used in order to liquefy the clots; three main drug families exist, which differ on the basis of their mode of action: tissue plasminogen activators, streptokinase and urokinase. Other drug substances do exist, but most of them are only efficient within the first hours of the symptoms, thus demonstrating that, although clot formation is reversible, it evolves over time and becomes increasingly irreversible in practice.

While thrombolysis is above all studied in the context of the abovementioned pathologies, it is also studied for the vascular accesses used in dialysis. Specifically, in order to have a blood flow which is sufficient for extracorporeal circulation in a circuit, an appropriate access, also called the vascular access, onto which the inlets and outlets of the circuit will be connected, needs to be prepared. There are mainly three accesses: fistulas, catheters and implants; they are fitted into the patient by means of surgery. They frequently (0.5-2 times per year for implants, 0.1-0.5 times per year for fistulas) become obstructed by clots. The publication by Quencer et al., "Hemodialysis access thrombosis, review article", Cardiovasc. Diagn. Ther. 2017; S299-S308 describes the various solutions, and the limitations thereof, which make it possible to eliminate clots from fistulas and implants, and how the diagnosis is established. The publication by Kennard et al., "Interventions for treating central venous haemodialysis catheter malfunction (Review)", Cochrane database of systematic reviews 2017, Issue 10. Art. No.: CD011953 discusses the various studies performed for treating catheters obstructed with clots. On reading these publications, it appears that several thrombolysis techniques, together with their respective advantages and drawbacks, are conceivable, but also that no one technique has proven to be consistently superior to the others.

The substances that may be used for dissolving the existing clots act in various ways and at various moments during the coagulation cascade, directly targeting the platelets, the fibrin or the interactions between the constituent components of the cascade, for example by reducing the $Ca^{++}$ concentration. Therefore, they are effective at various moments during the coagulation process, which process comprises numerous possible steps and pathways. By nature, the cases usually studied and described above relate to clots which have been formed for several hours or even several days. The means used and the results obtained in these cases may thus be very different from those observed in a blood circuit under circumstances within seconds or minutes of the clot formation.

Circuits for extracorporeal blood circulation always possess pressure measurements which are used to determine if the blood circulation forced through a pump proceeds as required. It is thus possible, and known, to detect a nascent coagulation in a circuit, for example by means of measuring the pressures upstream and downstream of a component such as a dialyser, or the pressure upstream of a blood clot filter placed to retain said clots before reinjecting the blood into the patient. Specifically, coagulated blood does not circulate, or not much so, and it at least partially obstructs the tubing in which it is present; it will therefore slow down the blood circulation, and if a pump is used to force the flow, the pressure difference will increase between the upstream part and that downstream from its position. When this happens, there is a "snowball" effect due to the rapid acceleration of the phenomenon, as the platelets stick to one another. In such cases, in common practice no means exist for continuing the treatment beyond a few minutes after detecting the presence of clots, and it is even not always possible to return the blood to its patient/donor before the circuit is completely obstructed.

The anticoagulation systems used for extracorporeal circulation circuits and described in the literature all focus on preventing coagulation by the injection, notably, of heparin or of citrate, according to models of varying complexity, the appropriateness of which must be reassessed either by the nursing staff, or automatically at least once every hour. When clots occur in the circuit, it would nonetheless be advantageous to liquefy said clots in order to be able to continue the blood circulation and the related treatments, rather than changing the circuit, as is usually done. However, the methods described above and used at the laboratory level or in the body of patients cannot be applied to blood circulation circuits, as these methods are either too slow or too complicated. De facto, a blood extracorporeal circuit is special from the point of view of the formation of clots, since the blood is, on the one hand, strongly activated and, to counterbalance this, strongly anticoagulated. Furthermore, it is possible in this case to rapidly detect the formation of clots and thus take action at an early stage of the coagulation cascade.

For example, patent application EP 1095666 describes a system which applies to a "haemofiltration" treatment, which measures parameters representing the flow of the blood and of the ultrafiltrate, extracted from blood through a filter, and adapts accordingly the predilution flow rate, which consists of a physiological solution provided upstream of the filter, for the main purposes of preventing fouling in the filter whilst automatically adjusting the volume of exchange. Said document describes the possible means for determining the state of the circulation in a circuit. Its application is, however, limited to a haemofiltration circuit which is necessary to remove the predilution. Specifically, rinsing a circuit via predilution requires the injection of large amounts of fluid, typically at a flow rate of at least 1 l/h, which cannot be accumulated in the patient and must thus be discarded. Moreover, predilution has essentially filter antifouling properties by reducing the blood viscosity and increasing the blood flow rate; it achieves a small reduction in coagulation by diluting the blood, and thus in the concentration of platelets which are then less likely to come into contact, but this effect is often not sufficient to prevent the formation of clots. This invention has the benefit of measuring the circulation conditions in a circuit used in haemofiltration, and variations thereof, to adapt the flow rate of a substance, the predilution, improving this circulation. However, it is not able to achieve the liquefaction of existing clots and requires the supply of large quantities of water, which must be removed from the circuit before returning the blood to the patient. Therefore, it is specific to one type of treatment, haemofiltration, which makes it possible to extract large quantities of water by filtration.

SUMMARY OF THE INVENTION

The inventor has observed that the addition of heparin when the blood starts to coagulate in a circuit is completely pointless, much like circulating physiological saline instead of blood.

The aim of the present invention is to remedy, at least partly, the abovementioned drawbacks.

To this effect, the present invention relates to an extracorporeal blood circulation device including a blood circulation circuit which comprises at least one blood extraction line and a blood return line, and also means arranged to circulate the blood in the circulation circuit, means for measuring at least one parameter influenced by the resistance to blood flow in the circulation circuit, and a control unit comprising calculation means arranged for the determination of at least one threshold value of said parameter, recording it in a memory, and then comparing the current value of said parameter with said recorded threshold value.

According to the invention, said device also comprises at least one source of blood clot liquefaction solution, injection means and one or more connecting lines for conveying said liquefaction solution into the circulation circuit. Furthermore, the control unit comprises means for driving at least one of said injection means of said liquefaction solution, and said control unit is arranged for actuating said driving means when said threshold value is exceeded, meaning that at least one clot has formed, said driving means being arranged so that the liquefaction solution is present in the circulation circuit in an amount and for a time predetermined to be necessary and at least sufficient to enable the liquefaction of the formed clot.

Said driving means will act according to parameters such as flow rate, time or volume, the main thing being that the amount of liquefaction liquid, determined for the volume of blood present in the circuit, and the time, determined by the mode of action of the liquefaction solution, are sufficient to liquefy the clots present in the circuit. As will be obvious to those skilled in the art, said driving means will act by actuating the means for circulating the liquefaction solution and/or the means for circulating blood, in order to ensure that said amount and said time are adhered to anywhere in the circuit.

Therefore, the driving means may also be arranged to control the means arranged to circulate the blood in the circulation circuit according to various scenarios, for example by reducing the blood flow rate in the circuit in order to leave more time for the action of the liquefaction solution, or by completely stopping the blood for a given time once the circuit has been filled with an amount, giving a concentration, which is estimated as being sufficient, of a liquefaction solution. Numerous other options of driving, known to those skilled in the art, are possible, for example the reproduction, at regular time intervals or after a particular event such as an interruption of the blood circulation means, of an injection of liquefaction solution in order to liquefy any nascent clot. The various scenarios are by no means exclusive and in practice they may be combined for the determination of the driving of the liquefaction liquid circulation means.

Advantageously, the, means for measuring at least one parameter influenced by the resistance to blood flow in the circulation circuit is arranged for measuring a pressure or a flow rate.

Preferably, the calculation means are arranged to compare a current value of said parameter with said recorded threshold value, according to a frequency sufficient to allow liquefaction of the clot being formed, i.e. preferentially once per second but at least once per minute.

Preferably, the liquefaction solution is made of water and of a component chosen from the group comprising citrate, urokinase, streptokinase, and mixtures thereof, present in an amount which is sufficient for liquefying a clot. Any other known or upcoming substance or mixture may of course be used in the liquefaction solution, as long as its effects on clots and any effects that are undesirable for the patient, are determined.

Advantageously, the device of the invention may also comprise means arranged to perform preventive anticoagulation.

Advantageously, the liquefaction solution comprises a component chosen from the group comprising citrate, urokinase, streptokinase and mixtures thereof. The liquefaction solution preferably comprises citrate.

The inventor has observed that the addition of citrate as a liquefaction solution having a concentration at least twice that of the concentration used for prevention makes it possible to liquefy clots, as long as this is done within the first minutes of the phenomenon gaining momentum. However, when the addition is performed by an operator, and is based on his or her personal and often late assessment, then it is often necessary to change the circuit which is already obstructed with clots.

Therefore, the present invention proposes a device or apparatus having a blood circulation circuit intended for any use (dialysis, ECC, apheresis, ECMO) as previously described, and which makes it possible first to detect that blood is in the process of coagulating, and secondly to perform liquefaction of the clots by injecting a substance, a small amount of which, ideally less than 100 ml, is sufficient for this purpose. Therefore, it enables the liquefaction of blood which has coagulated (i.e. blood which, from a liquid state, has turned into a solid to form a clot in the circuit) and thus continuation of the blood circulation without having to change the circuit.

BRIEF DESCRIPTION OF THE DRAWINGS

Other characteristics and advantages of the present invention will be apparent upon reading the following detailed description of several embodiments of the invention, given as non-limiting examples, with reference to the attached drawings, in which.

DESCRIPTION OF THE PREFERRED EMBODIMENTS

Figure 1:
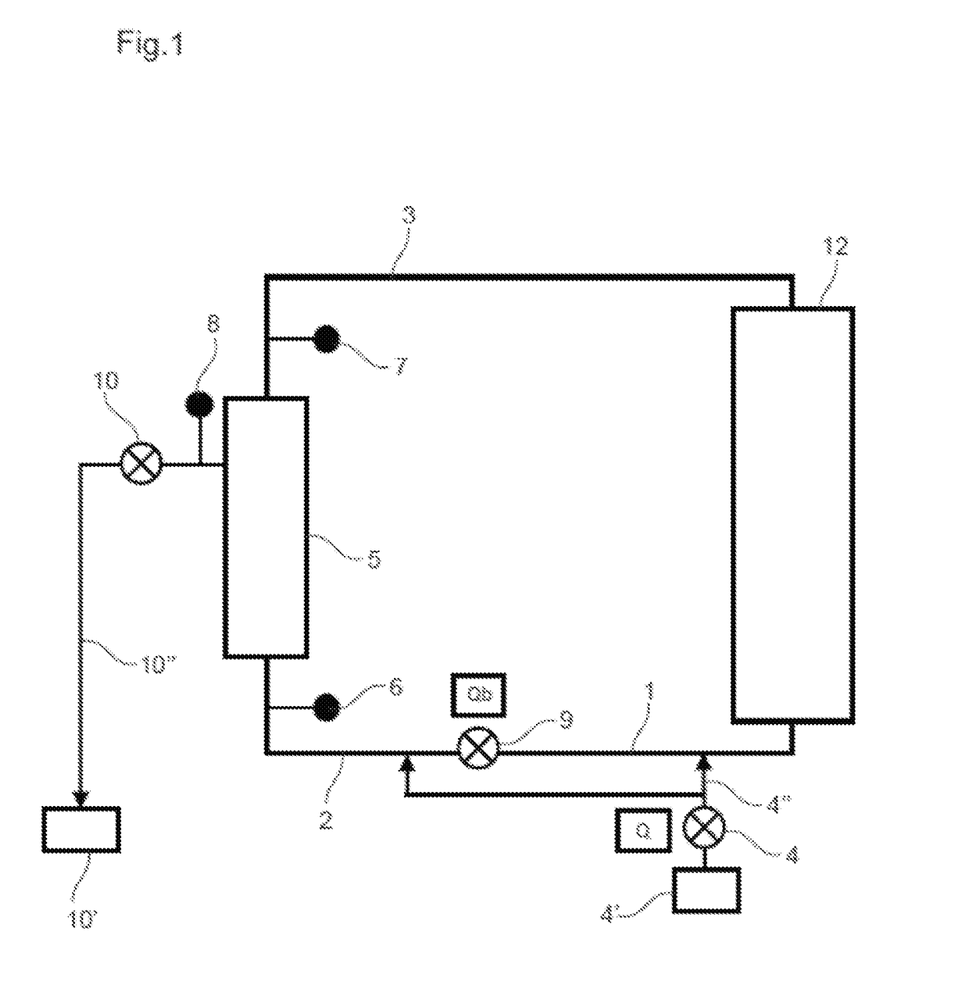
FIG. 1 represents a schematic view of an extracorporeal blood circulation device according to a particular embodiment of the invention.

An apparatus according to the present invention has, as shown in FIG. 1, an extracorporeal blood circulation circuit comprising at least one blood extraction line comprising a line 1 for the extraction of blood from the patient or donor, and a blood return line 3. Said circuit may be completed with a line 2 and blood modification means 5. The apparatus also comprises means 9 arranged to circulate the blood in the circulation circuit. On the circulation circuit, injection means 4 are placed for the injection of a fluid containing a solution 4' capable of liquefying blood clots in line 1 and/or line 2; this solution 4' may be contained in any type of reservoir such as a bag, a syringe or a bottle. Said injection means comprise a connecting line 4" and means arranged to circulate the liquefaction solution 4' in said connecting line 4", such as a pump 4.

The device may also comprise blood modification means 5, for example consisting of filters, dialysers, adsorption cartridges or an oxygenator. These means 5, which are not present in the case of a pure ECC, may in practice consist of several components, for instance a dialyser and an adsorption cartridge. Moreover, the apparatus may include means 6, 7, 8 for measuring at least one of the parameters influenced by the resistance to flow of blood in the circulation circuit. These measuring means may be pressure sensors or flow rate sensors 6 and/or 7 and/or 8, which are generally used to ensure that the circulation in the circuit is in line with expectations and notably that lines are neither disconnected nor bent. In the case of dialysis and apheresis, the apparatus may be completed with means for extracting fluid obtained from the blood modification means 5, said extraction means comprising a pump 10, a line 10", and rejection means 10'. Moreover, the blood circulation circuit is completed in practice by the usual, but not shown, means for protecting the patient or donor 12, for instance a blood leak detector or an air detector associated with a clamp, and other means for injecting solutions, for instance a syringe pump for preventive anticoagulation or means for the substitution of the extracted fluid. These means not shown are commonly known to those skilled in the art and are described in the literature; they may, needless to say, form part of the apparatus described in the present invention.

The fluid circulation means 4, 9, 10, used in the present invention as represented by the circuit in FIG. 1, may be in practice either peristaltic pumps, diaphragm pumps, centrifugal pumps, syringe pumps or clamps, which are well-known components used in applications requiring an extracorporeal blood circulation circuit. These means are completed with reservoirs, lines and connectors.

The essential components for the present invention are the blood circulation circuit consisting of lines 1 and 3, means for blood circulation 9, means for injecting a solution 4, 4', 4" and a control unit as described hereinbelow. The other components are optional for an apparatus according to the invention and may or may not be added according to the intended use of the blood circuit.

Figure 2:
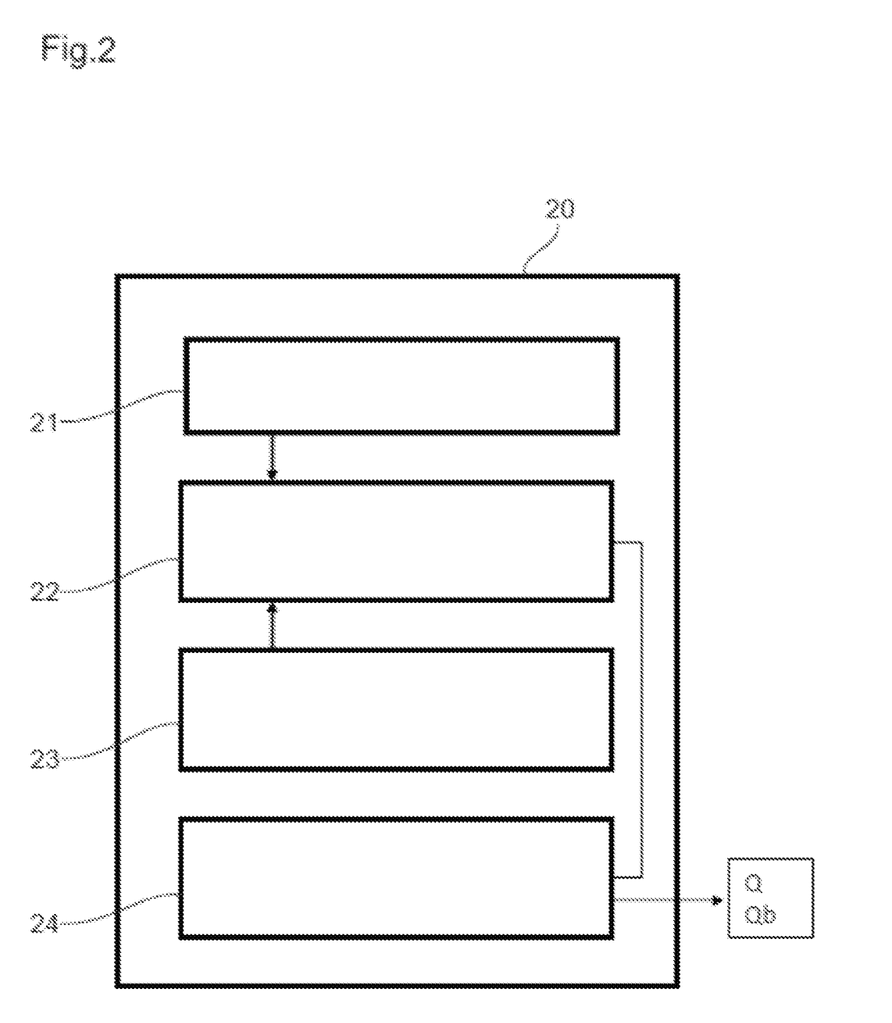
FIG. 2 is a block diagram of an exemplary embodiment of the control unit.

The apparatus according to the invention thus has a control unit 20, as shown in FIG. 2, consisting of a user interface 21 for displaying necessary messages and, if applicable, for inputing determinant values of the invention. The calculation means 22 act according to pre-established rules in order to liquefy clots and send the necessary messages to the user interface taking, when so required, information which is recorded in memory 23. The pre-established rules call upon known equations but may also include new conditions, notably high and low limits provided via the user interface 21. Among the known equations, mention may be made that a flow rate "Q" represented by pump 4 is associated with the liquefaction liquid 4'. The injected amount "M" per unit time "t" is given by multiplying the flow rate "Q" by the corresponding time, i.e. $M=Q*t$ whereas the injection time "T" may be calculated knowing the blood volume "V" on which an action is desired, for example 2×the volume included in the circuit, with: $T=V/Qb$, where Qb is the blood flow rate given by pump 9. The driving means 24 of the control unit will then control pumps 4 and 9 according to the performed measurements and calculations.

Figure 3:
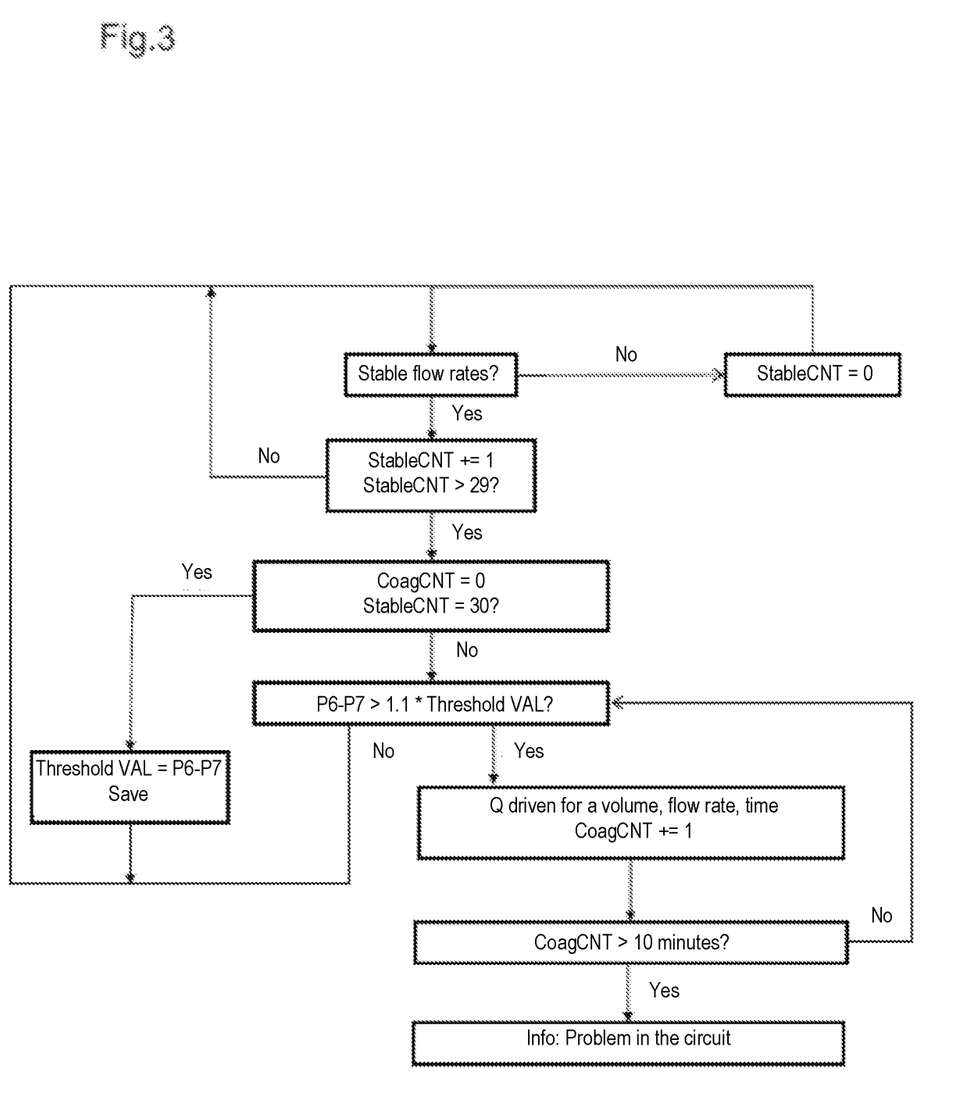
FIG. 3 illustrates a set of working operations that may be carried out by the control unit of FIG. 2.

The calculation unit of an apparatus according to the invention may run, for example, according to an algorithm as illustrated in FIG. 3. In a stable flow rate regimen, for example determined for a constant speed of the blood pump 9 over 30 seconds, the control unit 20 records the difference between pressure 6 and pressure 7 in memory 23, this difference being updated each time the stability conditions disappear, which initializes the stable time counter. When the measured difference increases relative to the one recorded, for example more than 10%, the control unit 20 drives pump 4 of liquefaction solution 4' at a flow rate and for a predetermined time for dissolving the developing clots, and it then checks that the difference returns below the desired 10% within the next 10 minutes. Otherwise, the control unit 20 informs the user, via the interface 21, that there is a problem in the circuit. Other algorithms are of course conceivable, the important thing being that they proceed by first determining somehow that clots are developing in the circuit, typically by using pressures or flow rates measured by 6, 7 or 8, and by applying rules as described, for instance, in patent application EP 1095666, and then injecting, for a predetermined time and flow rate, a solution capable of liquefying the existing clots. The time and flow rate may of course be replaced with other parameters. The means 6, 7 or 8 may be replaced or completed with predetermined time intervals or situations, for instance stoppage for more than 2 minutes of the blood circulation means which are known to be the frequent cause of clot formation.

As an illustration, the example of an apheresis performed with preventive anticoagulation which injects continuously, at a flow rate equal to 5% of the blood flow rate of 150 ml/min, a fluid containing a solution 4' with 4% citrate, pump 4 thus providing a flow rate of 7.5 ml/min, can be taken. The pressure difference 6–7 initially indicates 60 mmHg. When this difference is greater than 66 mmHg, pump 4 doubles its flow rate to inject no longer 5%, but now 10% citrate relative to the blood flow, and does so for 3 minutes, and the pump then returns to its initial flow rate and the control unit 20 checks that the difference 6–7 is lower than 63 mmHg from then on. In the same application, driving the pumps could be performed not by doubling the speed of pump 4 but by halving that of pump 9. This solution would have the advantage of not increasing the citrate dose injected into the patient, while at the same time providing the same citrate concentration in the blood and thus the same liquefaction effect.

The circulation of citrate is performed over 1-2 volume(s) of the circuit, i.e. over 200-400 ml in an example of apheresis or dialysis, which represents a pulse of between 16 and 40 ml of solution, that is to say a low volume relative to preventive anticoagulation. This pulse, when applied at the right moment, makes it possible for the treatment to be continued for as long as clinically indicated, and therefore to reduce the patient's blood losses and the associated transfusion risks. It is observed, with this example, that the means 4, 4' and 4" provided for the injection of the liquefaction solution may also be used for preventive anticoagulation, which has the advantage of reducing the necessary equipment and also the time required for its installation.

If preventive anticoagulation, i.e. that aimed at preventing the formation of clots in the circuit, were to be performed with means other than a citrate solute as in the above example, the situation would be the same and a citrate pulse would have the same effect.

A great number of other variants may be used for liquefying clots contained in an extracorporeal circulation; they all consist in injecting a liquefying solution at a given moment and for a time and volume determined as being necessary and sufficient. It is optimal that said given moment be determined based on the detection of clot formation with pressure or flow rate measuring means 6, 7 or 8, as this makes it possible to act each time, and only when, a clot is in the process of developing. However, a possible variant would consist in injecting the liquefying solution at predetermined time intervals, for example every 20 minutes, or on the basis of events, for example stoppage of the blood pump for more than 2 minutes, but this would not be optimal and would pose the risk of a late injection leading to a result identical to that of preventive anticoagulation.

Thus, another example would be that of a dialysis performed with preventive anticoagulation using heparin, which would be injected using a syringe pump (not shown). To comply with the invention, the dialysis apparatus would also include means 4, 4', 4" for injecting a solution containing 4% citrate which would be driven as described in the previous case, or a solution containing urokinase or a mixture of both which would be injected for 90 seconds so that all the blood contained in the circuit is mixed with the liquefaction solution before stopping pumps 4 and 9 for 3 minutes in order to allow time for the solution to act and to liquefy the clots. As a variant, rather than measuring only the difference 6–7, the control unit 20 could further measure the transmembrane pressure (TMP) defined by ((6+7)/2)–8) and drive pump 4 not only on the basis of the difference 6–7 but also on the basis of a TMP increase.

A third example would be an ECC not including preventive anticoagulation. In this case, pump 4 could be a syringe pump in which the 60 ml syringe would be filled with a solution including a mixture of 20% citrate and of streptokinase. When the pressure of the returning blood 7 increases, indicating the presence of a clot downstream, a 10 ml bolus is injected by the syringe pump, which can then liquefy 6 clots in succession, before informing the operator that the syringe needs refilling.

An essential advantage of the present invention is that it makes it possible, by comparison with the existing techniques, to significantly reduce the risks associated with the use of anticoagulants, as these can be dosed "a minima", any clots being detected and liquefied automatically by using a small amount of liquefaction solution, the latter being occasional and involving only the volume of blood contained in the circuit (which is typically 200 ml in the case of apheresis and dialysis) and not the cumulative volume of blood (typically 200 ml/min of blood flow rate, i.e. 12 l/h) or the volume of blood in the patient (about 5 litres for an adult weighing 70 kg). Thus, by proposing means enabling the liquefaction of clots, the invention makes it possible not only to use a minimum amount of anticoagulants, but also to avoid the drawbacks of a circuit containing coagulated blood.

The embodiment variants according to the invention apply to all the various configurations of extracorporeal circulation circuits; they include the possibility of using various possible solutions, comprising one or more substances capable of liquefying clots, and injecting them at various points in the circuit but preferably before blood pump 9.

The invention claimed is:

1. Extracorporeal blood circulation device including a blood circulation circuit comprising at least one blood extraction line (1) and a blood return line (3), means (9) arranged to circulate the blood in the circulation circuit, means (6, 7, 8) for measuring at least one of the parameters influenced by the resistance to flow of blood in the circulation circuit, and said device comprising a source of solution (4') for liquefying blood clots, means (4, 4") for injecting said liquefaction solution (4') into the circulation circuit (1, 3) and a control unit (20) comprising calculation means (22) arranged for determining at least one threshold value of said at least one parameter, recording the at least one threshold value of said at least one parameter in a memory (23), and comparing the current value of said at least one parameter with the recorded threshold value, and the control unit (20) comprising driving means (24) for driving said means (4) for injecting said liquefaction solution (4') into the circulation circuit (1, 3), and the control unit (20) is provided to actuate said driving means (24) for driving the injection means (4) when said threshold value is exceeded, indicating the presence of a clot, so that the liquefaction solution (4') is present in the circulation circuit in an amount and for a time predetermined to be necessary and sufficient for liquefying the clot(s) formed in said circuit.

2. The device according to claim 1, wherein the control unit (20) is arranged for determining or receiving from the user interface (21) at least one time interval, recording the at least one time interval in a memory (23), and comparing a standard value of time with said time interval to actuate the means (24) for driving the injection means (4) arranged to circulate the liquefaction solution (4') in said connecting line (4").

3. The device according to any claim 1, wherein the calculation means (22) control the driving unit (24), by reducing or stopping the flow of a blood pump (9), so that the liquefaction solution (4') is present for a time considered as sufficient in the circulation circuit.

4. The device according to claim 1, wherein the blood circulation circuit is completed by blood modification means (5) and a line (2).

5. The device according to claim 1, wherein the means (6, 7, 8) for measuring at least one of the parameters influenced by the resistance to flow of blood in the circulation circuit are arranged to measure a pressure.

6. The device according to claim 1, wherein the means (6, 7, 8) for measuring at least one of the parameters influenced by the resistance to flow of blood in the circulation circuit are arranged to measure a flow rate.

7. The device according to claim 1, further comprising means for performing preventive anticoagulation.

8. The device according to claim 1, wherein the source of solution (4') for liquefying blood clots and the means (4, 4") for injecting said liquefaction solution (4') into the circulation circuit (1, 3) are used for performing preventive anticoagulation.

9. The device according to claim 1, wherein the liquefaction solution (4') comprises a component chosen from the group comprising citrate, urokinase, streptokinase and mixtures thereof.

10. The device according to any claim 2, wherein the calculation means (22) control the driving unit (24), by reducing or stopping the flow of a blood pump (9), so that the liquefaction solution (4') is present for a time considered as sufficient in the circulation circuit.

11. The device according to claim 2, wherein the blood circulation circuit is completed by blood modification means (5) and a line (2).

12. The device according to claim 3, wherein the blood circulation circuit is completed by blood modification means (5) and a line (2).

13. The device according to claim 2, wherein the means (6, 7, 8) for measuring at least one of the parameters influenced by the resistance to flow of blood in the circulation circuit are arranged to measure a pressure.

14. The device according to claim 3, wherein the means (6, 7, 8) for measuring at least one of the parameters influenced by the resistance to flow of blood in the circulation circuit are arranged to measure a pressure.

15. The device according to claim 4, wherein the means (6, 7, 8) for measuring at least one of the parameters influenced by the resistance to flow of blood in the circulation circuit are arranged to measure a pressure.

16. The device according to claim 2, wherein the means (6, 7, 8) for measuring at least one of the parameters influenced by the resistance to flow of blood in the circulation circuit are arranged to measure a flow rate.

17. The device according to claim 3, wherein the means (6, 7, 8) for measuring at least one of the parameters influenced by the resistance to flow of blood in the circulation circuit are arranged to measure a flow rate.

18. The device according to claim 4, wherein the means (6, 7, 8) for measuring at least one of the parameters influenced by the resistance to flow of blood in the circulation circuit are arranged to measure a flow rate.

19. The device according to claim 5, wherein the means (6, 7, 8) for measuring at least one of the parameters influenced by the resistance to flow of blood in the circulation circuit are arranged to measure a flow rate.

20. The device according to claim 2, further comprising means for performing preventive anticoagulation.

\* \* \* \* \*